United States Patent [19]
Alvarez

[11] Patent Number: 4,756,866
[45] Date of Patent: Jul. 12, 1988

[54] NITROGEN DETECTION

[76] Inventor: Luis W. Alvarez, 131 Southampton Ave., Berkeley, Calif. 94707

[21] Appl. No.: 847,191

[22] Filed: Oct. 9, 1985

[51] Int. Cl.$^4$ .......................... G21G 1/12; G21H 5/00; G21K 5/10
[52] U.S. Cl. .................................................. 376/157
[58] Field of Search .............................. 376/157, 159

[56] References Cited

U.S. PATENT DOCUMENTS

| | | | |
|---|---|---|---|
| 3,662,882 | 5/1972 | Obermayer | 376/159 |
| 3,832,545 | 8/1974 | Bartko | 376/159 |
| 3,849,655 | 11/1974 | Martucci | 376/157 |
| 3,997,787 | 12/1976 | Fearon et al. | 376/159 |
| 4,031,388 | 6/1977 | Morita et al. | 376/157 |
| 4,251,726 | 2/1981 | Alvarez | 376/159 |
| 4,320,298 | 3/1982 | Buford, Jr. et al. | 376/157 |
| 4,338,520 | 7/1982 | Stewart | 376/157 |
| 4,428,902 | 1/1984 | Murray | 376/157 |

OTHER PUBLICATIONS

Int. J. Appl. Radiat. Isot, vol. 35, No. 11, 1984, pp. 1009–1021, Millen et al.
Radiochem. Radioanal. Letters 5/4–5/, pp. 217–222, 1970, Kapitza et al.
J. Applied Physics, vol. 45, No. 5, 5/74, pp. 2191–2200, Lightowlers et al.
Nucleonics, Sep. 1965, pp. 70–78, Tilbury et al.
*Encyclopedic Dictionary of Exploration Geophysics, 1974* Society of Exploration Geophysicists, Tulsa, Okla., by Sheriff.
JSR-85-505, 7/22/85, "Detection of Concealed Explosives", Alvarez et al., the Mitre Corp., Mclean, Va.
Physical Review, vol. 87, No. 12, p. 543, 1952, Panofsky et al.
Physical Review, vol. 75, No. 12, pp. 1815–1818, Jun. 1942, Alvarez.
J. of Applied Rad. & Isotopes, vol. 22, 1971, pp. 29–40.

Primary Examiner—Harvey E. Behrend
Attorney, Agent, or Firm—Townsend and Townsend

[57] ABSTRACT

A method and apparatus for detecting concentrations of nitrogen between 20% and 30% by weight such as is common in explosives is disclosed. A microtron having an output electron beam at a level below 45 MeV is targeted onto a typically tungsten target to provide gamma radiation levels. Deflection magnets adjacent to the target deflect the electron beam of the microtron to cause it to scan. Articles placed on a container containing suspect nitrogen are systematically scanned and output gamma radiation of 511 keV detected from nitrogen. Nitrogen concentrations and consequently expected concealed explosives are easily mapped in two or three dimensions, quantitatively.

12 Claims, 1 Drawing Sheet

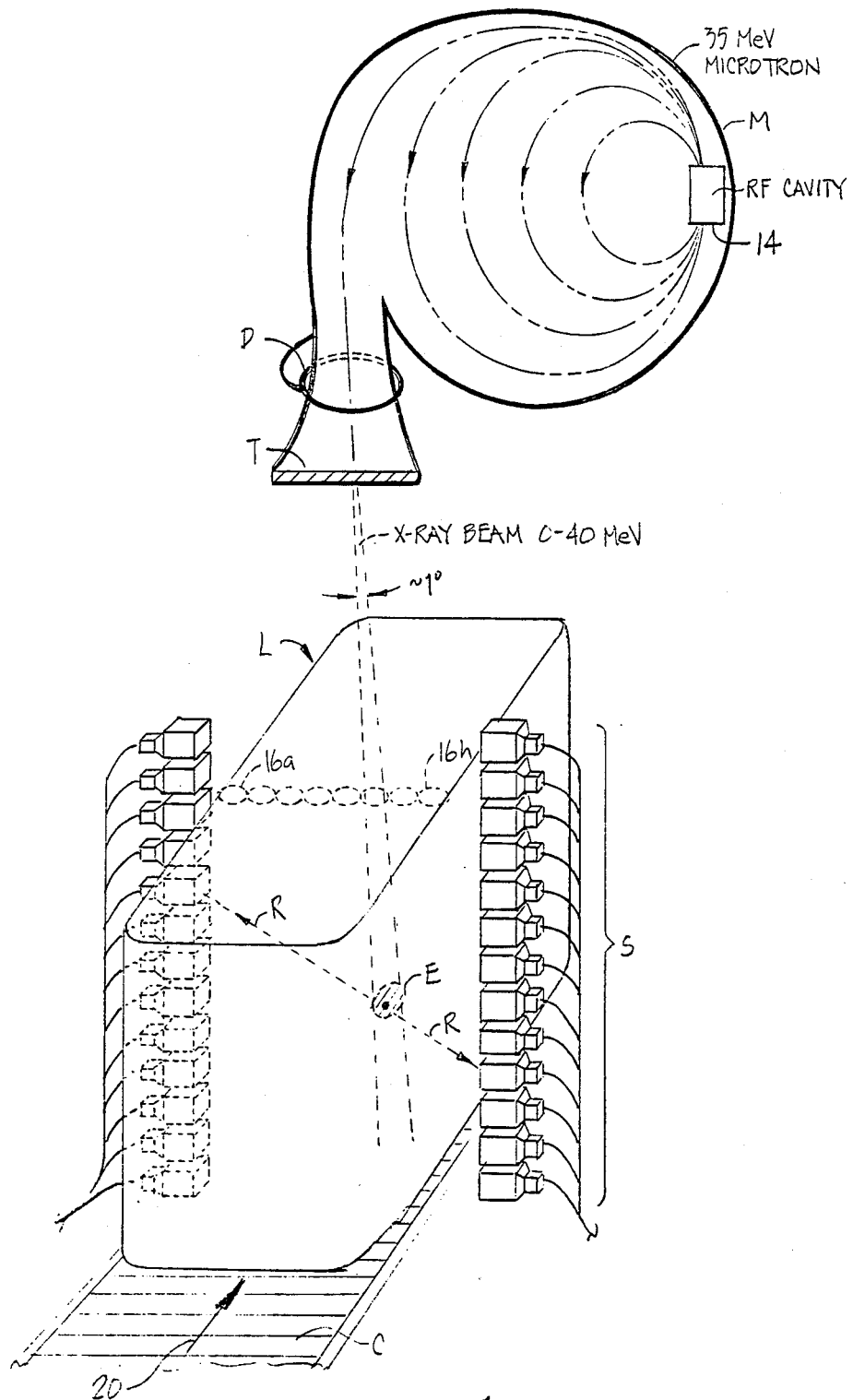
FIG—1.

NITROGEN DETECTION

BACKGROUND OF THE INVENTION

It has been proposed to tag all commercially produced explosives with a unique material that can be easily identified. Vapor taggants of considerable cleverness have been investigated. However, they have two strikes against them, namely the required cooperation of explosives manufacturers (common to any taggant program; explosives manufacturers are particularly resistant to introducing any substance that reduces the performance or reliability of the explosive), and the ease with which the system can be circumvented by appropriately sealing the bomb.

This second drawback can be circumvented if a taggant is used that can be detected by its nuclear properties, or by some other penetrating probe. I have previously suggested that explosives or detonators that have been partially deuterated are easily detected by irradiation with 4 MeV gammas. This takes advantage of the fact that deuterium has the second lowest threshold for (gamma,n), and has the additional advantage that explosive performance is not sacrificed, since deuterated X has the same chemistry as ordinary X. The estimated cost is of the order of 10 cents per detonator or stick of dynamite. This scheme is adaptable to area searches (when everyone has been evacuated), where, with the longer integration time permitted, it is possible to search a whole airplane at once. Unfortunately, all tagging schemes have the distinct disadvantage that they have no applicability to scenarios that are driven by forces of international terrorism.

With almost no exceptions, all explosives current in use contain large amounts of nitrogen, typically between 20% and 35% by weight. Although there are some common articles that also contain nitrogen (animal products and some synthetics), they generally have nitrogen present in lower concentrations and being generally more spread out.

A known method exploits the nuclear reaction produced by the capture of slow neutrons by nitrogen nuclei, giving off an unusually high energy (10.8 MeV) gamma ray that is easily detected by scintillation detectors. The parcel to be examined passes through a shielded enclosure in which it is subject to slow neutrons while being examined for gamma emission. In order to "see" whether the source of gamma rays is compact (a bomb) or spread out (a nylon sweater), a number of detectors are used to form a crude image of the gamma emitting object, i.e., the shape of the nitrogen-containing material. It must always be crude, since slow neutrons do not go on straight lines but diffuse through the package being examined.

As additional related prior art, I discovered $^{12}N$ and observed its then record-holding short half life (12 ms) in about 1949. The decay of this isotope produces back to back 511 keV annihilation radiation. Nitrogen 12, Physical Review, 1949.

The reaction $^{14}N(gamma, 2n)^{12}N$ was seen by Panofsky et al. in about 1952. This reaction has received little, if any, attention since discovery in so far as I am aware.

SUMMARY OF THE INVENTION

This apparatus and method exploits that reaction whose cross-section includes the production of 511 keV annihilation radiation from the decay of an exceedingly short-lived isotope of nitrogen produced by irradiating ordinary nitrogen with high energy x-rays of about 40 MeV. This takes advantage of the fact that the x-ray source emanating from a microtron is a narrow beam, which can be electrically scanned over the parcel in order to image the nitrogen inside. This allows high resolution imaging of the contents of parcels by an improvement on the method of "positron emission tomography." This disclosed apparatus and method appears to make possible the determination of the mass of nitrogen in each two inch cube of the bag's volume, in two seconds, with the ability to re-examine the bag in 16 seconds, and similarly determine the mass of nitrogen in each one inch cube of the bag. If that potential can be realized, I do not see any way in which ordinary explosives could be undetected, in amounts sufficient to cause appreciable damage to a commercial aircraft.

Advantages and Disadvantages

The advantages of this method are: (1) Detection cannot be prevented by encapsulating, sealing, or wrapping the explosive, since detection does not depend on a sample of vapor given off by the explosive; (2) Detection cannot be prevented by shielding the explosive against neutrons or x-rays; (3) Detection does not depend on taggants that must be included when the explosive is manufactured; (4) All currently used explosives can be detected; (5) Photographic or x-ray film will not be fogged; (6) The systems are fast - as little as 1 to 2 seconds per package.

The disadvantages of this method are: (1) Nitrogen is not *unique* to explosives, therefore compact concentrations of nitrogen (for example, a six-inch cube of nylon) will cause false alarms; (2) The apparatus is large (perhaps as large as a small room) and expensive (more than $100K); (3) Exotic nitrogen-free explosives will escape detection.

DESCRIPTION OF THE FIGURES

FIG. 1 shows an apparatus for automated parcel screening in accordance with this disclosure.

DESCRIPTION OF THE PREFERRED EMBODIMENTS

X-Ray Probe

Referring to FIG. 1, the apparatus and method of this invention is schematically illustrated. A 35 MeV microtron or equivalent electron accelerator M with an Rf cavity 14 generates electron radiation. These electrons are directed at a tungsten target T and conventionally deflected by deflection magnets D and the resulting pencil beams of x-rays are scanned into discrete beams scanning luggage L passing through the explosive detector. The successive beams scan the areas 16A through 16H, here respective two-inch areas in the luggage.

Explosive E within the luggage L emits annihilation radiation R in the form of two oppositely-directed photons with energy 511 keV. This radiation is picked up by two stacks of two-inch wide bismuth germanate or sodium iodide scintillation detectors S, which can be longer than two inches in the direction of motion of the luggage. Resolution of the luggage L in a single plane normal to the suitcase is thereby determined as the intersection of two lines: the x-ray beam line and the line traced out by the oppositely directed 0.511 MeV photons. A conveyor C conveys luggage in the direction of arrow 20 through the apparatus of this invention. Consequently, the luggage is mapped in three dimensions.

The reaction $^{14}$N(gamma, 2n)$^{12}$N has the right characteristics to permit mapping. First, the isotope $^{12}$N is extremely short-lived (11 millisecond half-life). Second, the produced annihilation radiation is back-toback (i.e. precisely opposite in directions). By using oppositely disposed scintillation detectors to detect simultaneous annihilation events, the precisely opposite back-to-back 511 keV x-rays can be accurately traced. The traced rays, when combined with the positional information of the scanning beam, produce the "position emission tomography" to gain a non-invasive three-dimensional scan. (I use the terms x-rays and gamma rays interchangeably; they are indistinguishable once they are emitted.)

The radionuclide $^{12}$N has an unusually short half-life (11 milliseconds) for decay by positron emission. The positron stops and annihilates, producing as signature a pair of back-to-back 511 keV gammas that are easily recognized by their energy and geometry. $^{12}$N can be produced from $^{14}$N by a (gamma, 2n) reaction, with threshold of 30.64 MeV, and an unknown, but finite, cross-section which however is certainly less than a millibarn. To produce the reaction I irradiate the parcels with a pencil beam of 35–40 MeV x-rays, produced by bremmstrahlung when a 35–40 MeV electron beam from a microtron accelerator M strikes a tungsten target T. The opening angle of the gammas is about one degree, which means that no collimation is needed and the full output of the gamma source can be used. The resulting gamma beam is steered by magnetically deflecting the electron beam before it strikes the tungsten target.

As I will show later, there are a few competing sources of annihilation radiation, but those that do exist have much longer half lives, and, consequently, lower counting rates. Thus, to scan a parcel I produce a short (typically 2 microseconds) pulse of gammas at some beam position, then, after a few hundred microseconds (avoiding prompt radiation and allowing time for the detectors to recover), I spend 12 milliseconds looking for back-to-back annihilation gammas from any $^{12}$N that was produced. The irradiating beam is then moved to the next pixel and the process repeated. In combination with the parcel's motion, the irradiating beam scans two dimensions, and the two linear arrays of annihilation radiation detectors image the third (see FIG. 3). I thus accumulate a nitrogen "image" of almost 2000 pixels resolution in two seconds, from which I can declare the parcel as either "safe" or "suspicious." In the latter case I either examine the contents manually, or back it up, and rescan it at one eighth the original speed. This could give complete tomographic information, for the 14,000 one-inch pixels in the bag. (I use the word "pixel" in a nonstandard way to denote volume elements, rather than the usual projected area elements.)

Basic Design

FIG. 1 shows a possible arrangement for automated parcel screening. A 35 MeV electron beam is produced in a "microtron" accelerator, and deflected onto a tungsten target. The resulting gamma beam, with nearly flat power spectrum up to the electron energy of 35 MeV and opening angle of approximately 2 degrees, irradiates the parcel, which is being carried along on a conveyor. As the parcel moves along, the pulsed irradiation is scanned perpendicular to the motion. I will assume that the accelerator optics gives a pencil beam always smaller than 2" in diameter, and that successive pulses of radiation are stepped in increments of 2" across the parcel, using 8 such beam locations to cover 16" of package width before beginning the next transverse scan.

The detector array consists of two stacks of sodium iodide, or bismuth germanate scintillators each, constructed with 2" crystals and photomultipliers, placed on each side of the parcel stream. For the one inch resolution mentioned above, one could use twice as many of such detectors. These additional detectors would also work as well at the two inch resolution most often used. The detector stacks are oriented parallel to the beam direction, as shown, and are used to determine the coordinate of an annihilation event along the beam direction (1 dimension). When combined with the known beam position (2 dimensions), this gives the origin of the event in 3 dimensions, to a resolution set by the detector size and beam diameter, in this case 2".

A full-size suitcase (16"×24"×36") would be scanned in the following way: The suitcase is carried along the conveyor, moving in the direction of its longest dimension. The beam scans repeatedly across the small dimension, irradiating 8 positions spaced 2" apart. Each beam position takes about 12 ms (2 µs irradiation, 12 ms detection), thus each traverse along the small dimension takes 0.1 second. For a 36" long bag, 18 such traverses are needed, taking a total of 1.8 seconds. The bag contents are thus images in 3 dimensions at 2" resolution, a total of 8×12×18=1730 pixels.

Signal and Background Count Rates and Signatures Calculation of Expected Signal The expected count rate for a package containing some explosive can be calculated. In particular, let there be a 2"×2"×2" volume of explosive somewhere in the suitcase of unit density and 30% nitrogen by weight. The signature of that pixel, which contains less than 5 ounces of explosive (i.e., four pounds of explosive would occupy 15 contiguous pixels of similar signature) can be set forth. I assume the geometry and beam parameters just described, irradiated by a microtron with 2 µs pulses of M mA, with M now to be calculated.

The 35 MeV, M mA electron beam from the microtron has a flux of 6M×10$^{15}$ electrons/sec, and a peak power of 35M kilowatts. The conversion efficiency to gammas by bremmstrahlung is given by $$\text{gammas in } [E_1, E_2] \text{ per electron} = \sim 0.8 \int_{E_1}^{E_2} \frac{dE}{E}$$
$$= \sim 0.12, \text{ from 30 MeV to 35 MeV.}$$

The 5 cm cube of explosive contains 125 gm of explosive of 30% nitrogen content, i.e., 38 gm of nitrogen or 1.6×10$^{24}$ nitrogen atoms. The (gamma, 2n) crosssection has been detected, but not measured, so I will assume it to be the conservative value of 10$^{-5}$ bars or 10$^{-29}$ cm$^2$. Then the total cross-section of nitrogen atoms in the 5 cm cube is 1.6×10$^{24}$×10$^{-29}$, or 1.6×10$^{-5}$ cm$^2$, thus 6.4×10$^{-7}$ of the gammas incident of the 25 cm$^2$ face will produce $^{12}$N and hence positrons. Therefore the number of $^{12}$N nuclei produced per second, during irradiation of that pixel, is 6.4×10$^{-7}$×M×6×10$^{15}$×0.12=4.6×M×10$^8$ per second, or $9.2 \times M \times 10^2$ in a 2 microsecond pulse. One might at first think that only half of those would be countable, since the active counting time is very nearly one half life. But essentially all are countable, but in the next few scans of neighboring pixels. This will produce a slight "smearing" of the image, which will not seriously degrade it, and can easily be eliminated by a simple "deconvolvement algorithm."

What these last two words mean is that if we had a single two inch cube of nitrogen in an otherwise empty bag, the cube would appear to be smeared out in the direction of the x-ray scan, with each subsequent x-ray line showing a two inch cube with one half the counts of the previous one. We can say that mathematically, the image of the single cube has been smeared downward by a known exponential "smearing function," or convolved with that smearing function. Since the function is a known one, it is easy to deconvolve the smeared image back to a nearly prestine one, with almost no smearing. The deconvolution can be done by a simple subtraction routine, as anyone skilled in the art will appreciate, and it can be done as the bag is moving, so no time will be lost in the process. And now that the concept of deconvolution has been introduced, it may be possible to scan the whole bag more rapidly, by counting for a time shorter than one half life, and using the deconvolution routine at all times. So, to simplify matters, I will assume all $^{12}N$ nuclei will contribute to the tomograph of the bag, so that number is $9.2 \times M \times 10^2$.

I will now assume the counters to be 2" wide by 6" long (in the transport direction), and of a thickness to give each one a counting efficiency of 50%. I will assume that the useful area of each group of counters is $6'' \times 10''$, and that their average distance from the $^{12}N$ atoms is 10". Then, the geometrical efficiency for detecting a pair of annihilation gamma rays is 60 square inches/$4\pi \times 100$ square inches$=4.8 \times 10^{-2}$. I now multiply this number by the square of the detection efficiency, since I must detect two gamma rays. I end up, then, with an overall detection efficiency of $1.2 \times 10^{-2}$. Since I want to observe 100 counts, to give a 10% accuracy in the assay for nitrogen in each pixel, I need a number of produced $^{12}N$ atoms equal to $100/1.2 \times 10^{-2}=8300$. I can now evaluate the current M, in milliamperes, from the equation $9.2 \times M \times 10^2=8300$, so $M=9$, and we need 9 milliamperes. So the peak power of the beam is 35 MV$\times$9 mA$=315$ kilowatts. This is a reasonable power, from the simplest high power microwave generator known, the cavity magnetron. It takes several hundred kilowatts of microwave power to excite the microwave cavity in the microtron to produce the strong electric fields needed to accelerate electrons to the extent that each circular orbit is one wavelength longer than the previous one. The fact that 2 megawatt magnetrons are available, and that microtrons have been built that accelerate beam currents of 50 milliamperes shows that the parameters assumed and calculated in this section are "reasonable," and "not forced." There is no need to calculate any of these numbers any more accurately, since they are all based on an assumed cross-section for the formation reaction that was purposely chosen smaller than it probably is, and quoted only to the nearest power of 10.

We note that the signal per pixel is not a rapid function of the pixel side D, if I assume the time per suitcase inspection to vary inversely with $D^3$. The "optical depth" of nitrogen in a pixel goes as D, the detector solid angle is independent of D, and the number of beam positions per bag face goes as $D^{-2}$. So, all combined, we get the same number of counts per one inch cube as we do per two inch cube. This is quite a surprising and potentially useful property of the new system.

Interferences

I must consider the production of interfering radiation from other chemical elements inside typical packages. In this case there are two possibilities, namely (a) the production of other positron emitters by gamma irradiation, and (b) the production of $^{12}N$ from the only other important atomic species, namely oxygen.

I am helped in case (a) by the fact that the lifetime of $^{12}N$ is unusually short (11 ms), so that, for a given production cross-section, its decays relative to those of a competing positron emitter are more frequent by the ratio of lifetimes. So, for example, $^{10}C$ has a lifetime of 19.3 seconds, and could be made from $^{12}C$ by a (gamma, 2n) reaction with a threshold of 31.8 MeV; because of the ratio of lifetimes, its decays are down relative to $^{12}N$ by a factor of 1750 for the same production cross-section. In fact, its cross-section is so small that it is listed as "0," which can be interpreted as being less than 0.1 mb. Likewise, positron emitters of the other light elements all either have lifetimes longer than a minute, or thresholds over 40 MeV, and are thus probably unimportant.

There are positron emitting isotopes of heavier elements that can be formed from the abundant stable isotope by (gamma,n) with threshold in the 10-20 MeV range, and with shorter lifetimes. For example, $^{27}Si$ with a half life of 4.1 sec, $^{31}S$ (2.6 sec), $^{34}Cl$ (1.5 sec), and $^{38}K$ (0.9 sec).

The production of $^{12}N$ from other normally abundant atomic species would be a serious problem, because it is its short lifetime that I am taking advantage of in my detection scheme. It can't be made in a primary reaction by gammas from anything of Z lower than the 7 of nitrogen, since a gamma ray can only knock out neutral or positively charged objects. It can, of course, be made in a (gamma, 2n) reaction from $^{14}N$, with threshold of 30.64 MeV; this is the reaction I plan to use. It can also be made in a gamma,(n,$^3H$) reaction from $^{16}O$ with a threshold of 35.1 MeV. Since oxygen is abundant, this reaction must be avoided, which is why I use a gamma spectrum that cuts off at 35 MeV. $^{12}N$ can also be made in a gamma,(3n,$^4$He) reaction from $^{19}F$ with a threshold of 45.5 MeV, which obviously cannot take place here.

It will be understood that the $^{16}O$ reaction need be of significant proportion to interfere with the $^{12}N$ production desired from interaction with $^{14}N$. Therefore, I believe that energy levels up to 40 MeV will suffice for the practice of this technique. Only experiment can set the allowable upper limit of x-ray energy.

I could make $^{12}N$ from $^{12}C$ in a secondary reaction by protons resulting from a reaction of the form $X(p,n)Y$. The (p,n) reaction has a threshold of 17.4 MeV, so only (gamma,p) photoproduction reactions that make protons of energy greater than 17.4 MeV are significant. I cannot make such protons by photoproduction on H, since momentum cannot be conserved. Protons from photoproduction on deuterium are below threshold, since it costs 2.2 MeV to break up the deuteron so, with 35 MeV gammas, I have only 32.8 MeV to split equally between proton and neutron giving 16.4 MeV to each.

Photoproduction on carbon or oxygen can make protons above threshold (19 MeV from $^{12}C(gamma,p)^{11}B$; 22.7 MeV from $^{16}O(gamma,p)^{15}N$). But those protons quickly lose energy, and drop below the 17.4 MeV threshold for the (p,n) reaction I wish to avoid in a very short distance. For example, 22.7 MeV protons have lost 5 MeV in 0.2 mm of unit density carbon; 19 MeV protons have fallen below threshold in 0.06 mm. Thus there appears to be no important mechanism for production of $^{12}N$ from other elements as long as the gamma energy is kept below 35 MeV. (Experiments may well show that the microtron energy can be raised above 40 MeV with no deleterious effects, since the emission of a $^3H$ nucleus, as needed to make $^{12}N$ from $^{16}O$, would be expected to occur infrequently.)

Shielding of the disclosed apparatus and method will be required. An example of suitable shielding can be found in FIG. 1 and related text of my U.S. Pat. No. 4,251,726 entitled "Deuterium Tagged Articles such as Explosives and Method for Detection Thereof." Specific placement and amounts of shielding can be made by the routineer.

What is claimed is:

1. Nitrogen concentration detection apparatus useful for the detection of nitrogen concentration in an article containing suspect nitrogen comprising:
   a source of x-ray energy exceeding 30.64 MeV, said x-rays causing the following reaction

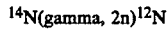
   $^{14}N(gamma, 2n)^{12}N$ in nitrogen in said article but having insufficient energy to cause a significant reaction $^{16}O(gamma, n^3H)^{12}N$, said significant reaction being that which would interfere with $^{12}N$ production desired from interaction with $^{14}N$;
   at least two gamma ray detectors aligned near the path of said generated x-ray for detecting the 511 keV annihilation gamma radiation produced by the reaction of $^{14}N(gamma, 2n)^{12}N$; and
   means for conveying said article proximate said x-ray source and said gamma ray detectors.

2. The apparatus of claim 1 and wherein the x-ray energy source has an energy level of less than 40 MeV.

3. The apparatus of claim 1 and including means for scanning said x-rays from said x-ray energy source.

4. The apparatus of claim 1 and including two linear arrays of gamma ray detectors aligned parallel to the path of said generated x-rays, one array disposed on one side of said article and the other detector disposed on the opposite side of said article to give a three-dimensional tomographic image of the nitrogen content of the article.

5. A method of scanning a series of conveyed articles for randomly placed nitrogen concentrations in the order of 20% to 30% by weight comprising the steps of:
   providing an x-ray source having x-rays exceeding 30.64 MeV in the range sufficient to cause a significant reaction

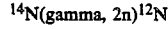
   $^{14}N(gamma, 2n)^{12}N$ but insufficient to cause a significant reaction $^{16}O(gamma, n^3H)^{12}N$, said significant reaction being that which would interfere with $^{12}N$ production desired from interaction with $^{14}N$;
   irradiating a suspect article to determine the presence of nitrogen with radiation sufficient to cause the reaction $^{14}N(gamma, 2n)^{12}N$ where gamma is x-radiation, and n is a neutron;
   detecting delayed annihilation radiation from said $^{14}N(gamma, 2n)^{12}N$ in the range of 511 keV on opposite sides of said articles for simultaneous scintillation events; and
   moving said article and beam relative to one another to quantitatively map said article in three dimensions, relative to its nitrogen content.

6. The method of claim 5 and wherein said moving step includes conveying said article.

7. Method of claim 5 and wherein said mapping includes pulsating said x-radiation incident upon said article and examining said article for 11 milliseconds after each pulsation for said reaction.

8. Nitrogen concentration detection apparatus comprising in combination:
   a high energy electron source having an output electron beam in the order of 35 MeV;
   a target for said high energy electron source to produce x-radiation in the range exceeding 30.64 MeV;
   deflection magnets adjacent said target for deflecting the electron beam of said microtron to cause said electron beam to scan;
   a conveyer suitable to transport an article containing suspect nitrogen through the path of said electron beam scan; and
   a stack of scintillation detectors for detecting the 511 keV annihilation gamma radiation produced by the reaction $^{14}N(gamma, 2n)^{12}N$ where:
   gamma is x-radiation;
   n is a neutron; and
   $^{14}N$ and $^{12}N$ are isotopes of nitrogen.

9. The apparatus of claim 8 and wherein said high energy electron source has an energy level less than 40 MeV.

10. The apparatus of claim 1 and wherein said source of x-rays is an electrom beam from a microtron or linear accelerator impacting a heavy element target.

11. The apparatus of claim 8 and including first and second stacks of solid state detectors on opposite sides of said conveyor.

12. Nitrogen concentration detection apparatus useful for the tomographic mapping of nitrogen concentrations in an article containing suspect nitrogen comprising:
   a source of x-ray energy exceeding 30.64 MeV, said x-rays causing the following reaction

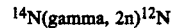
   $^{14}N(gamma, 2n)^{12}N$ in nitrogen in said article but having insufficient energy to cause a significant reaction $^{16}O(gamma,n^3H)^{12}N$; said significant reaction being that which would interfere with $^{12}N$ production derived from interaction with $^{14}N$
   means for conveying along a conveyor path said article by said scanning x-ray beam; and,
   means for scanning said source of x-rays across said article and said conveyor path;
   first and second linear arrays of annihilation radiation detectors aligned parallel to the path of said generated x-rays for detecting the 511 keV annihilation gamma radiation produced by the reaction of $N(gamma, 2n)^{12}N$, one array disposed on one side of a said conveyor path and the other array disposed on the opposite side of said conveyor path whereby a tomographic plot of the nitrogen in said articles can be made.

* * * * *